United States Patent
Eberle et al.

(10) Patent No.: US 9,375,729 B2
(45) Date of Patent: Jun. 28, 2016

(54) CASSETTE AND SYSTEM COMPONENT INSERTABLE INTO A CENTRIFUGE IN COOPERATION WITH THE CASSETTE

(75) Inventors: Klaus-Günter Eberle, Tuttlingen (DE); Roland Biset, Leuven (BE); Wilfried Mertens, Leuven (BE)

(73) Assignees: Terumo BCT, Inc., Lakewood, CO (US); Andreas Hettich GmBH & Co. KG, Tuttlingen (DE)

( * ) Notice: Subject to any disclaimer, the term of this patent is extended or adjusted under 35 U.S.C. 154(b) by 1022 days.

(21) Appl. No.: 13/521,142

(22) PCT Filed: Jan. 5, 2011

(86) PCT No.: PCT/EP2011/050094
§ 371 (c)(1),
(2), (4) Date: Nov. 13, 2012

(87) PCT Pub. No.: WO2011/083120
PCT Pub. Date: Jul. 14, 2011

(65) Prior Publication Data
US 2013/0130883 A1    May 23, 2013

(30) Foreign Application Priority Data
Jan. 8, 2010   (DE) .......................... 10 2010 000 752

(51) Int. Cl.
*B04B 5/04* (2006.01)
*A61M 1/36* (2006.01)
*A61M 1/02* (2006.01)

(52) U.S. Cl.
CPC ............ *B04B 5/0428* (2013.01); *A61M 1/3693* (2013.01); *A61M 1/0209* (2013.01); *A61M 2205/12* (2013.01); *B04B 2005/0435* (2013.01)

(58) Field of Classification Search
CPC   A61M 1/3693; A61M 1/0209; B04B 5/0428; B04B 2005/0435
See application file for complete search history.

(56) References Cited

U.S. PATENT DOCUMENTS

| 5,456,845 A | 10/1995 | Nishimura et al. |
| 5,543,062 A | 8/1996 | Nishimura |
| 5,734,464 A | 3/1998 | Gibbs |

(Continued)

FOREIGN PATENT DOCUMENTS

| DE | 196 22 050 A1 | 5/1996 |
| DE | 100 65 283 A1 | 12/2000 |

(Continued)

OTHER PUBLICATIONS

International Search Report dated Sep. 25, 2008 for PCT/EP2008/056926.

(Continued)

*Primary Examiner* — Timothy Cleveland
(74) *Attorney, Agent, or Firm* — John R. Merkling

(57) ABSTRACT

The invention pertains to a cassette (2) comprising a product conveying path (1, 1a, 1b) and a positioning means (3a, 3b) engageable with a counter-piece on a centrifuge having a rotor for separating blood components or on a system component (4) arranged in a centrifuge. The positioning is effected such that a section of the product conveying path (1, 1a, 1b) is aligned with a section of the centrifuge or the system component arranged in the centrifuge. Furthermore, a tube connected with bags is accommodated in the product conveying path (1, 1a, 1b).

12 Claims, 8 Drawing Sheets

(56) References Cited

U.S. PATENT DOCUMENTS

| | | |
|---|---|---|
| 5,795,317 A | 8/1998 | Brierton et al. |
| 6,234,989 B1 | 5/2001 | Brierton et al. |
| 6,361,518 B1 | 3/2002 | Brierton et al. |
| 7,166,217 B2 | 1/2007 | Holmes et al. |
| 7,194,087 B2 | 3/2007 | Luginbill et al. |
| 7,981,019 B2 | 7/2011 | Holmes et al. |
| 2002/0085957 A1 | 7/2002 | Moore et al. |
| 2003/0176267 A1 | 9/2003 | Eberle |
| 2004/0026341 A1 | 2/2004 | Hogberg et al. |
| 2008/0220959 A1 | 9/2008 | Holmes et al. |
| 2010/0170858 A1 | 7/2010 | Eberle et al. |
| 2011/0053201 A1 | 3/2011 | Eberle et al. |

FOREIGN PATENT DOCUMENTS

| | | |
|---|---|---|
| DE | 11 2004 000 569 T5 | 3/2006 |
| DE | 103 16 598 B4 | 5/2008 |
| DE | 102007000308 A1 | 12/2008 |
| DE | 102007000309 A1 | 12/2008 |
| DE | 102007000310 A1 | 12/2008 |
| EP | 0499891 A1 | 8/1992 |
| EP | 0616816 A2 | 9/1994 |
| EP | 1351772 B1 | 12/2001 |
| EP | 1512464 A2 | 3/2005 |
| EP | 1557187 A1 | 7/2005 |
| GB | 2174149 A | 10/1986 |
| WO | 02053292 | 7/2002 |
| WO | 03089027 | 10/2003 |
| WO | 2004069310 A2 | 8/2004 |
| WO | 2007024550 | 3/2007 |
| WO | 2010061863 A1 | 6/2010 |

OTHER PUBLICATIONS

International Search Report dated Sep. 25, 2008 for PCT/EP2008/056923.

International Search Report dated Oct. 14, 2008 for PCT/EP2008/056925.

International Search Report; International Application No. PCT/EP2011/050094; International Application Filing Date Jan. 5, 2011; Mail date May 2, 2011.

Written Opinion; International Application No. PCT/EP2011/050094; International Application Filing Date Jan. 5, 2011; Mail date May 2, 2011.

International Preliminary Report on Patentability; International Application No. PCT/EP2011/050094; International Application Filing Date Jan. 5, 2011; Date of completion of this report Apr. 4, 2012.

Millipore Corp.: MulitiScreen Assay System, Centrifuge Alignment Frame, User Guide, 2008.

IV-IV

CASSETTE AND SYSTEM COMPONENT INSERTABLE INTO A CENTRIFUGE IN COOPERATION WITH THE CASSETTE

TECHNICAL FIELD

The invention relates to a cassette used as cover for accommodating blood bags for a cartridge of a centrifuge for separating blood components, and a system component insertable into such a centrifuge in cooperation with the cassette.

BRIEF DISCUSSION OF RELATED ART

In transfusion medicine, the so-called blood component therapy has established itself since the beginning of the nineties. This means that, instead of a whole blood conserve, only those blood components required by the individual patient are administered to said patient. This separate administering of the individual blood components makes it possible that one single blood conserve optimally helps an average of 1.8 patients.

The essential blood components are
the red blood cells in the so-called erythrocyte concentrate, which are transfused in order to maintain the oxygen supply after severe loss of blood,
the blood platelets in the thrombocyte concentrate, which are administered in cases of coagulation disturbances (haemophilia), and
the blood plasma, which is administered in cases of coagulation disturbances and volume deficits.

Apart therefrom, blood plasma is an essential basic component for the production of many medicaments.

The separation of the individual blood components, which is defined as cell separation/isolation, is known to be effected by treating the blood in a centrifuge. By means of centrifuging, the individual blood components are separated from each other, and can then be separately filled into the respective containers for further use.

Documents DE 10 2007 000 308 A1, DE 10 2007 000 309 A1 and DE 10 2007 000 310 A1 already reveal a cartridge for use in a centrifuge for separating blood components and a respective centrifuge as well as a respective method. According to these documents, a cartridge comprises an intermediate wall and a cover. The intermediate wall separates a blood bag area disposed radially inside from a product area disposed radially outside. In an installation position of the cartridge, the cover is located above the blood bag area. The cover is connected to the intermediate wall pivotally at one point, and detachably at a second point. In this way, the blood bag area is freely accessible by a lateral turning away of the cover. For loading the cartridge with a blood bag, the cover is opened, a blood bag and a product bag are inserted into the respective chambers, and a connecting tube is inserted along a product conveying path. Moreover, photosensitive sensors are arranged along the product conveying path and are used to establish the composition of the product while the product is obtained; when a specific composition is reached, measures are taken for terminating the obtaining of the product. However, loading of the cartridge may only be effected manually, which renders it time- and cost-consuming. Besides, there is the possibility that the product is destroyed upon a faulty insertion of the connecting tube, since the sensors do not react timely.

Therefore, the known means need to be improved such that, on the one hand, faulty loading is avoided and, on the other hand, time is saved.

BRIEF SUMMARY

According to the invention, a cassette is provided, comprising a product conveying path in the form of a passage and a positioning means engageable with a counter-piece on a centrifuge or on a system component arranged in a centrifuge such that a section of the product conveying path is aligned with a section of the centrifuge or the system component arranged in the centrifuge. A tube connected with bags is accommodated in the product-conveying path.

Thus, according to the invention, cassettes with the already inserted tube and two or more bags (one blood bag and at least one product bag) attached to the tube can be supplied to a user in the form of a kit. Thus, after a blood collecting process, the cassette comprising the tube and the bags can be inserted into a system component of a centrifuge, or directly into the centrifuge to perform a centrifugation process in which the blood in the one bag is separated and at least one of the separated blood components is transferred into the second bag.

After this centrifugation process has been completed, it is merely necessary to replace the cassette present in the centrifuge by a new one and to subject the old cassette to further processing. In this respect it is noted that, in general, any number of cassettes can be subjected to the centrifugation process. Preferably a number of six cassettes is processed simultaneously in the centrifuge.

Since the tubes and bags are replaced together with their related cassette, a remarkable reduction of dead time is achieved.

The exact alignment of the connecting means with the counter-piece makes it possible to reach an exact alignment of the product conveying path with the respective section of the centrifuge or the system component. This ensures that photosensitive sensors arranged in the section of the system component can detect the product flowing through the product conveying path anytime. Thus, appropriate reactions, e.g. for terminating the production process are promptly possible, without delay. In particular, the section of the product-conveying path and/or tube arranged directly adjacent to the positioning means can be exactly positioned to be directly adjacent to the counter piece where the sensors are provided. Furthermore, due to the positioning means, it is ensured that an axis of the sensors substantially intersects a central axis of the product conveying path at a right angle.

Advantageously, the cassette may comprise a lower part and an upper part which are connected to each other by snap elements or other means. It is also possible that the positioning means is only formed in the lower part, only in the upper part, or in both. Other means in terms of the invention may e.g. be screw joints and/or rivet joints or bonded joints.

Preferably, the positioning means is provided in the form of one or plural bars arranged in the direction of one or plural sections of the product conveying path. The bars can be arranged in a window. Such an arrangement can be easily manufactured, and can easily establish a form-fit connection with an appropriately formed counter-piece.

Advantageously, at least one shut-off device for interrupting a product flow can additionally be provided at one or plural sections of the product conveying path. The shut-off device makes an abrupt termination of the production process possible. The maximally possible portion of the desired product, e.g. thrombocytes, can be gained before the product is contaminated by undesired blood components.

Advantageously, the at least one shut-off device can be integrated into the lower part or into the upper part of the cassette, and can be operated directly from outside the cassette. This allows a quick and safe operation of the shut-off device without the danger of a failure, which may otherwise occur by a faulty insertion of the shut-off device. The operation of the shut-off device can be effected manually or mechanically, e.g. by means of actuating members operated pneumatically, hydraulically or electronically.

Advantageously, the at least one shut-off device can be provided in the form of one or two tube clamps, which can be operated separately from each other.

Besides, the cassette may comprise connecting means for being connected to a cartridge, which can be accommodated in the centrifuge or the system component arranged in the centrifuge. Accordingly, the cassette fulfills a function as cover of the cartridge.

Advantageously, the cassette according to the invention is accommodated in a system component for arrangement in a centrifuge for separating blood components, with a rotor rotatable around a hub. The system component comprises a counter-piece which can be engaged with a positioning means of the cassette. In this way, an exact positioning of a section of the product conveying path to a section of the system component is ensured.

The counter-piece may be provided in the form of an elevation having one or plural grooves in the wall sections of which one or plural sensors are arranged. Preferably, these are photosensitive sensors/photosensors.

Additionally, the system component can comprise an operating means for operating a lock-off device disposed in the cassette. The operating means can preferably be provided in the form of a centrally arranged, long lever having two ends and two short, L-shaped levers arranged at the ends of the long lever. Each end of the long lever is directly operable by a first piston, or indirectly by a second piston and a leg of the short, L-shaped lever.

Preferably, the cassette and the system component can be used in a centrifuge for separating blood components, having a rotor of a centrifuge rotatable around a hub. The system component is accommodated in the rotor, or integrated into the same. Moreover, a cartridge can be incorporated into the system component, and this cartridge can be provided with a cassette loaded with a blood bag and a product bag. The cassette is used as cover for a blood bag area of the cartridge.

The use of a cassette according to the invention and the system component according to the invention allows to obtain one or also plural blood products, such as plasma, erythrocytes, or thrombocytes. This may be obtained particularly in that a microprocessor can be provided in the system component to be used for controlling and monitoring the product extraction process.

Then, by means of the microprocessor, particularly the detection results of the sensors can be processed and the operations of the shut-off devices can be carried out accordingly. Advantageously, the microprocessor in the system component can furthermore be connected to another microprocessor accommodated in the rotor of the centrifuge, which is adapted to carry out the control and the monitoring of the entire product extraction process.

BRIEF DESCRIPTION OF THE DRAWINGS

Further advantages of the invention can be seen from the description of a currently preferred embodiment and the Figures attached. Referring to the Figures.

DETAILED DESCRIPTION

Figure 1:
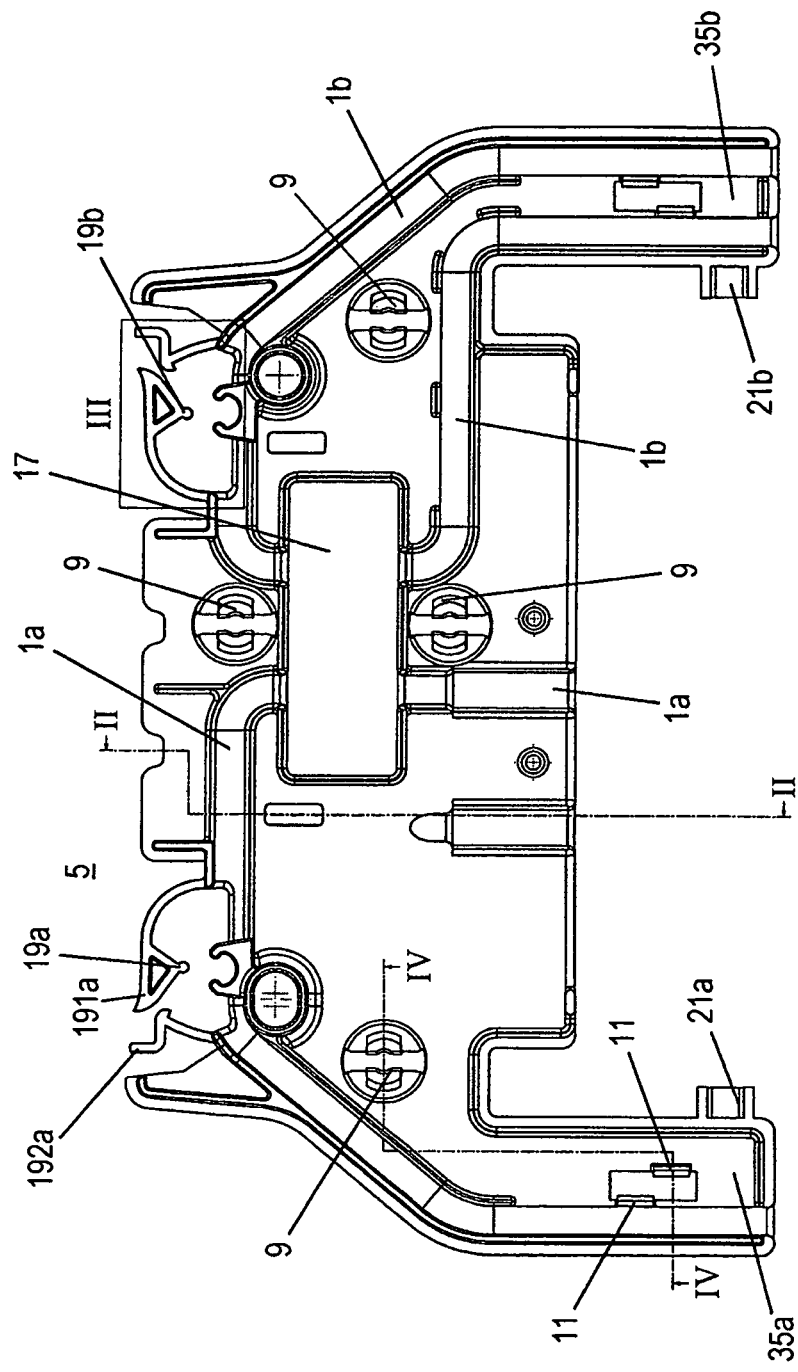
FIG. 1 shows a top view of a lower part of a cassette according to the invention.
Figure 2:
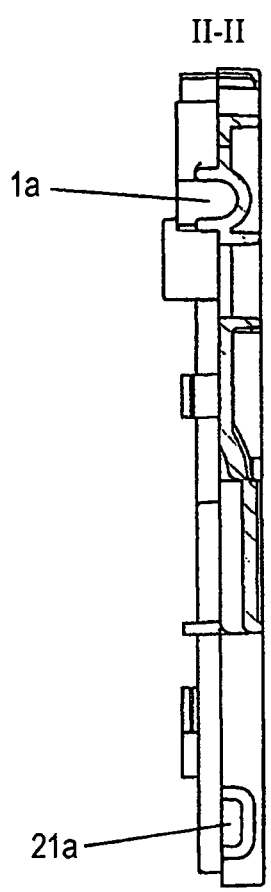
FIG. 2 shows a sectional view along a line II-II in FIG. 1.
Figure 3A:
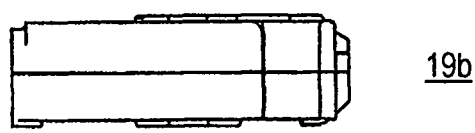
FIGS. 3a and 3b show a top view and a view of a detail III from FIG. 1, respectively.
Figure 3B:
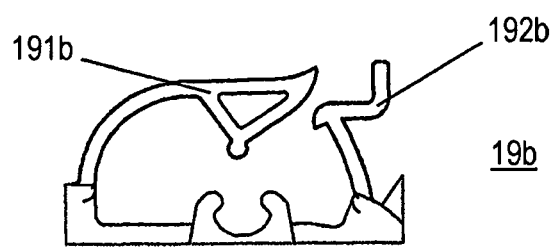
Figure 4:
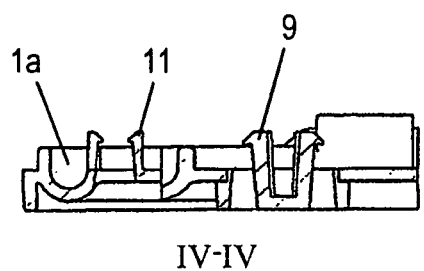
FIG. 4 shows a sectional view along a line IV-IV in FIG. 1.
Figure 5:
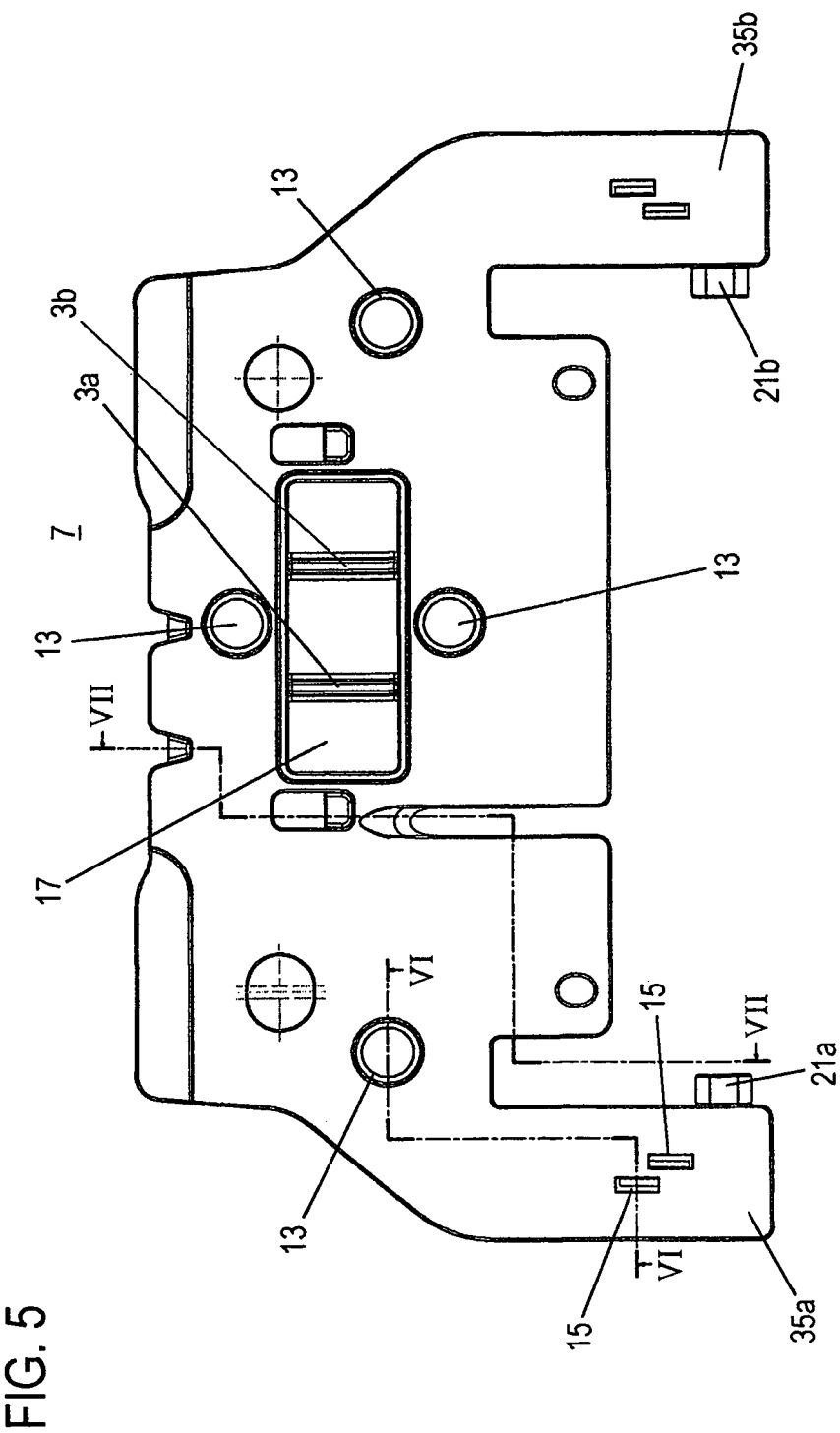
FIG. 5 shows a top view of an upper part of a cassette according to the invention.
Figure 6:
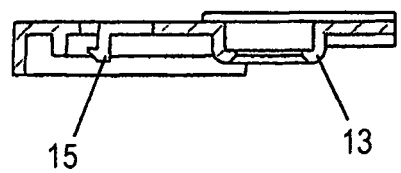
FIG. 6 shows a sectional view along a line VI-VI in FIG. 5.
Figure 7:
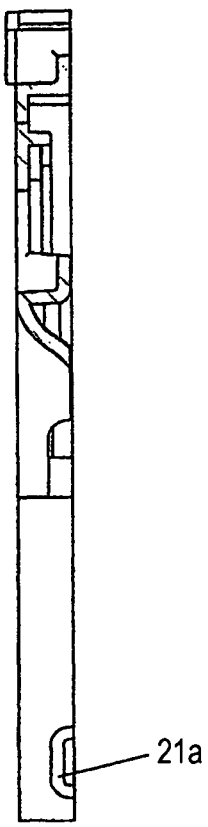
FIG. 7 shows a sectional view along a line VII-VII in FIG. 5.
Figure 8:
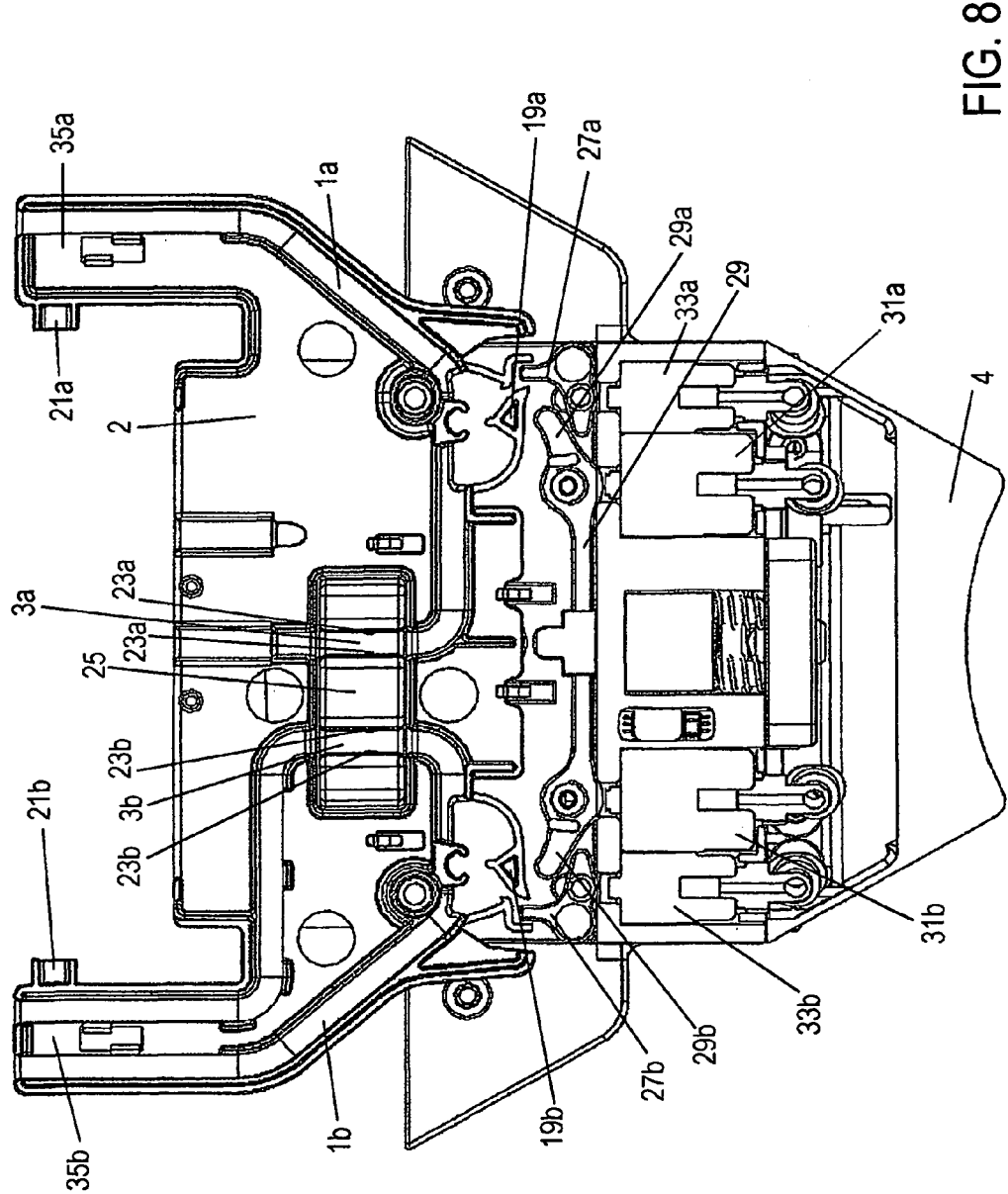
FIG. 8 shows a view of a cassette according to the invention, said cassette being provided in a system component according to the invention.

A currently preferred embodiment of the invention is described by means of FIGS. 1 to 8.

A cassette 2 according to the embodiment is composed of a lower part 5 and an upper part 7 which are connected to each other by means of snap elements 9 and 13, and 11 and 15, respectively. The upper part is made of a transparent material. Besides, as can be seen from the Figures, the cassette 2 is provided approximately in the form of a rectangle having two arms 35a, 35b.

The lower part 5 as well as the upper part 7 of the cassette 2 comprises a window 17 in a central area of the rectangle. Moreover, in the upper part 7, two bars 3a, 3b are formed to be used as positioning means according to the invention. The bars 3a, 3b extend along a partial section of a product-conveying path 1.

A channel-type passage 1 is formed as product-conveying path 1 in the lower part 5. The passage 1 is divided into two sections 1a and 1b. At one edge of the lower part 5 opposite the arms 35a, 35b, two tube clamps 19a, 19b are integrated into the lower part 5.

A tube (not shown in the Figures) provided with a blood bag, a filter and a product bag is laid in the product-conveying path 1 such that the tube is conducted from the blood bag disposed between the arms 35a, 35b to the first section 1a, along the bar 3a, through the tube clamp 19a arranged in the first section 1a further to the arm 35a. The tube then emerges from the arm 35a, leads to the filter, and enters via the second arm 35b the second section 1b of the passage 1. Then, the tube is led along the bar 3b, through the tube clamp 19b and again the arm 35b, in order to emerge from the same towards the product bag.

At each of its arms 35a, 35b, the cassette 2 comprises a projection 21a, 21b disposed inside, which is used to detachably fix the cassette to a non-represented cartridge similar to the one in documents DE 10 2007 000 308 A1, DE 10 2007 000 309 A1 and DE 10 2007 000 310 A1. The blood bag, the filter and the product bag are then accommodated in appropriate chambers of the cartridge. The cassette 2 replaces a cover in the said applications.

Together with the cassette 2, the loaded cartridge is inserted into a system component 4 that is arranged in a centrifuge. An elevation 25 in which two grooves are formed is provided in a section of the system component 4. Photosensitive sensors 23a, 23b are inserted into the inner walls of each groove.

If the cassette 2 is disposed in the system component 4, the elevation 25 is engaged in a form-fit connection with the window 17, and the bars 3a and 3b with the grooves formed in the elevation 25. The sections of the tube extending along the bars 3a, 3b are disposed directly below the bars 3a, 3b, whereby the contents of the tube can be exactly registered by the photosensitive sensors 23a, 23b. The first photosensitive sensor 23a is assigned to the first section 1a of the product-conveying path 1, whereas the second photosensitive sensor 23b is assigned to the second section 1b of the product-conveying path 1. The optical axes of the photosensitive sensors 23a and 23b substantially intersect the central axis of the product conveying path (the tube) at a right angle.

Since the tube does not have to be inserted into the cassette 2 any more, but the cassette is already delivered together with the readily laid tube including blood bag, filter and product bag, a faulty insertion of the tube or a displacement of the tube that would lead to a faulty registration by the sensors can be reliably excluded.

Thus, it is possible, due to the interaction of the cassette according to the invention with the system component, to obtain a blood product by means of the method disclosed in document DE 10 2007 000 309 A.

According to the embodiment, the rotor of the centrifuge is designed for six system components 4 having one cartridge each. After all cartridges loaded with cassettes 2 have been inserted, the centrifuge is started. By means of the centrifugal force, the desired separation of the blood components is effected. Since the "buffy coat" diluted by an additive solution is in the blood bag, the lighter components of it will remain radially inside, whereas its heavier components, i.e. the red blood cells, collect outside.

In order to transport the desired blood component—according to the embodiment, these are the platelets (thrombocytes)—in high quality, i.e. without the admixture of other blood cells, from the blood bag, the separation of the components will be followed by a slight pressure being applied onto the blood bag by means of a pressure pad, so that, after the previously closed tube clamps 19a, 19b have been opened, the solution rich in platelets begins to rise into the tube disposed in the passage 1. The solution rich in platelets is led through the tube into the filter designed as a leukocyte filter, and is further conducted therethrough.

In the leukocyte filter, the undesired leukocytes, i.e. the white blood cells, are removed. Due to the arrangement of the tube with the filter, the filtration is effected against the centrifugal force. Thus, heavier blood components, such as unintentionally transported red blood cells, are trapped in a filter-inlet chamber positioned radially outside.

After having passed the leukocyte filter, the solution rich in platelets continues flowing through the tube laid in the second section 1b of the passage 1 into a product bag, in which it is collected. Preferably, the product bag is already formed as final storage bag for the product.

In order to remove any air that might be present in the filter, the flow speed is kept low for a certain volume quantity at the beginning of the product transfer, thereby enabling the filter to fill with the blood product reliably and completely. After the transfer of this specific volume quantity, the conveying speed for a specific second volume quantity is increased by means of an appropriate control of the pressure pad. While this second volume is transported, there is hardly any risk that red blood cells contaminate the blood product (here: the thrombocyte concentrate). Should this nevertheless happen, this small number of red blood cells are collected in the lower and outer area of the filter, due to the tube being guided from radially outside and below into the filter, and due to the effect of the centrifugal force.

After the second volume has been transferred, the first photosensor 23a is activated and the flow speed of the blood product in the tube is reduced.

When the first photosensor 23a detects a predetermined proportion of red blood cells in the thrombocyte-rich solution, it outputs a signal by means of which the flow speed is again reduced. Furthermore, the second photosensor 23b disposed behind the filter is activated.

During this phase, also a rather large number of red blood cells can enter the filter and even pass therethrough until the second photosensor 23b detects a predetermined proportion of red blood cells in the blood product and outputs a signal for terminating the cell separation process. By this signal, the tube clamps 19a, 19b are closed by operation of the ends 29a, 29b of a long lever 29 by means of pistons 31a, 31b, so that the red blood cells in the filter are reliably separated from the thrombocyte concentrate in the product bag.

As an alternative to the termination by the second photosensor 23b, the cell separation process can also be terminated after a certain period of time has elapsed after the activation of the second photosensor 23b.

In the embodiment, altogether six cartridges are provided in the centrifuge. The above-described control of the cell separation process in a cartridge 1 by means of a pressure pad, the opening and closing of the tube clamps 19a, 19b, and the process control by means of the two photosensors 23a, 23b enables a continued cell separation in the cartridges of the other system components, since the described process control takes place individually for each combination of cartridge and system component.

The control of the process is effected by a microprocessor provided in the system component, said microprocessor processing the detection/registration results of the sensors 23a, 23b and accordingly controlling the opening and closing of the tube clamps 19a, 19b by operating the levers 31a, 31b and 33a, 33b, respectively. Besides, the microprocessor is connected to a microprocessor arranged in the hub of the rotor for controlling the centrifuge and monitoring the microprocessors in the individual system components.

When the above-mentioned process is carried out, a precise operation of the tube clamps 19a, 19b is required for ensuring an optimum yield while simultaneously avoiding a contamination of the product. For operating the tube clamps 19a and 19b integrated in the lower part 5 of the cassette 2, the invention provides, in the system component, an arrangement having a centrally arranged long lever 29 and L-shaped, short levers 27a, 27b arranged at the two ends 29a and 29b of the long lever 29. The ends 29a, 29b of the long lever are disposed between a leg of the short lever 27a, 27b and a closing arm 191 of the tube clamp 19a and 19b, respectively.

At its central section, the long lever 29 is fixed to the system component 4. The short levers 27a, 27b are pivotally supported around the intersection of the two legs of the "L". The entire lever arrangement is disposed along the edge of the cassette 2, on which the tube clamps 19a, 19b are arranged when the cassette is inserted into the system component.

Pistons 31a, 31b, 33a, 33b, which are suitably arranged in the system component 4, are used for operating the levers 27a, 27b and 29. The pistons 31a, 31b directly act on the respective end 29a, 29b of the long lever. The pistons 33a, 33b directly act on a leg of the short levers 27a and 27b, respectively, said leg being disposed between the pistons 33a and 33b and the respective ends 29a, 29b of the long lever 29.

Since the ends 29a, 29b of the long lever 29 are disposed directly opposite the closing arm 191 of the tube clamps 19a and 19b when the cassette is inserted, an operation of the piston 31a or 31b leads to the closing of the respective tube clamp 19a or 19b. Since, in turn, an operation of the pistons 33a, 33b acts on the one leg of the rotatably supported, short levers 27a and 27b, respectively, this operation leads to a twisting of the levers 27a and 27b, respectively. The leg disposed between the pistons 33a and 33b acts on the end 29a or 29b of the long lever 29, whereas the other leg of the short lever 27a or 27b acts on an opening arm 192 of the tube clamp 19a or 19b, thereby opening the same. The indirect operation of the ends 29a, 29b of the long lever serves to exclude that the tube clamp bursts open too suddenly or too wide, so that problems e.g. due to the tube clamps getting jammed can be avoided.

The invention has been described by means of a currently preferred embodiment, but is not restricted thereto in any way, but only defined by the scope of the claims attached.

The invention claimed is:

1. A cassette comprising:
   a product conveying path; and
   a positioning means engageable with a counter-piece on a centrifuge having a rotor for separating blood components or on a system component arranged in the centrifuge such that a section of the product conveying path is aligned with a section of the centrifuge or the system component arranged in the centrifuge,
      wherein a tube connected with bags is accommodated in the section of the product conveying path;
      wherein the positioning means is provided in the form of one or plural bars arranged in the direction of the section of the product conveying path, and the one or plural bars are arranged in a window.

2. A cassette according to claim 1, comprising a lower part and an upper part, wherein the positioning means is formed in the lower part or in the upper part, or in both.

3. A cassette according to claim 2, wherein the lower part and the upper part are connectable to each other by a connecting means and the product conveying path is provided in the form of a passage.

4. A cassette according to claim 1, wherein at least one shut-off device for interrupting a product flow is provided on the product conveying path.

5. A cassette according to claim 4, wherein the at least one shut-off device is integrated into a lower part or into an upper part of the cassette.

6. A cassette according to claim 4, wherein the at least one shut-off device is provided at a rim of the cassette and is directly operable from outside the cassette.

7. A cassette according to claim 4, wherein the at least one shut-off device is provided in the form of one or two tube clamps, which can be operated separately from each other.

8. A cassette according to claim 1, wherein the cassette comprises connecting means for establishing a connection with a cartridge accommodating the cassette, said cartridge being adapted to be accommodated in the centrifuge or in the system component arranged in the centrifuge.

9. A system comprising a centrifuge for separating blood components and a cassette for being arranged in said centrifuge for separating blood components, the centrifuge comprising:
   a rotor rotatable around a hub, and
   a counter-piece,
      wherein the counter-piece is provided in the form of an elevation having one or plural grooves in the wall sections of which one or plural sensors are arranged, and
the cassette comprising:
   a product conveying path; and
   a positioning means engageable with the counter-piece on the centrifuge for separating blood components or on a system component arranged in the centrifuge such that a section of the product conveying path is aligned with a section of the centrifuge or the system component arranged in the centrifuge,
      wherein a tube connected with bags is accommodated in the product conveying path;
      wherein the positioning means is provided in the form of one or plural bars arranged in the direction of the section of the product conveying path, and the one or plural bars are arranged in a window.

10. The system according to claim 9, further comprising an operating means for operating a lock-off device disposed in the cassette.

11. The system according to claim 10, wherein the operating means is provided in the form of a centrally arranged, long lever having an end and at least one short, L-shaped lever arranged at the end of the long lever, the end of the long lever being directly operable by a first piston, or indirectly by a second piston and a leg of the short, L-shaped lever.

12. The system according to claim 9, wherein the one sensor or the plural sensors are formed as light sensitive sensors, and by engaging the positioning means of the cassette with the counter-piece, a central axis of the tube accommodated in the product conveying path of the cassette is exactly aligned to the optical axis or optical axes of the light sensitive sensor or of the light sensitive sensors.

* * * * *